United States Patent [19]

Miller

[11] 3,998,230
[45] Dec. 21, 1976

[54] HAIR TRANSPLANT PROCESS
[75] Inventor: Paul W. Miller, Atlanta, Ga.
[73] Assignee: Hairegenics, Inc., Atlanta, Ga.
[22] Filed: Oct. 22, 1974
[21] Appl. No.: 516,887
[52] U.S. Cl. .................................. 128/330; 3/1
[51] Int. Cl.² .................... A61B 17/34; A61F 1/00
[58] Field of Search ............... 3/1; 128/330, 214.4, 128/347

[56] References Cited
UNITED STATES PATENTS

| 2,906 | 1/1843 | Sage | 128/218 R |
|---|---|---|---|
| 1,059,631 | 4/1913 | Popovics | 128/330 |
| 3,062,214 | 11/1962 | Maxwell | 128/330 |
| 3,406,685 | 10/1968 | May | 128/214.4 |
| 3,596,292 | 8/1971 | Erb et al. | 3/1 |
| 3,699,969 | 10/1972 | Allen | 128/330 |
| 3,817,250 | 6/1974 | Weiss et al. | 128/347 X |
| 3,893,445 | 7/1975 | Hofsess | 128/347 X |

*Primary Examiner*—Channing L. Pace
*Attorney, Agent, or Firm*—Robert B. Kennedy

[57] ABSTRACT

A method is disclosed for implanting hair into human skin comprising the steps of inserting an end of a hollow outer needle into skin to form a pit in the surface thereof, sliding an inner needle within the outer needle to position an end of the inner needle supporting a bulbous end of a hair within the skin pit adjacent the end of the outer needle, and extracting the outer and inner needles from the skin pit.

Apparatus is also disclosed for implanting hair into human skin which apparatus comprises a hollow outer needle having a relatively sharp end for piercing skin, a hollow inner needle slidably disposed within the hollow outer needle and having a centrally apertured relatively blunt end for receiving a hair therethrough and for supporting a bulbous hair end on the surface thereof, and means for moving the inner needle blunt end between positions remote and positions closely adjacent the outer needle sharp end.

Hair implantation apparatus is further described comprising a needle having a slot formed in an injection end thereof from which a passageway extends. A hairlike filament is loosely positioned within the needle passageway with an anchor at one end thereof in the shape of an arrowhead slidably positioned within the needle slot.

6 Claims, 34 Drawing Figures

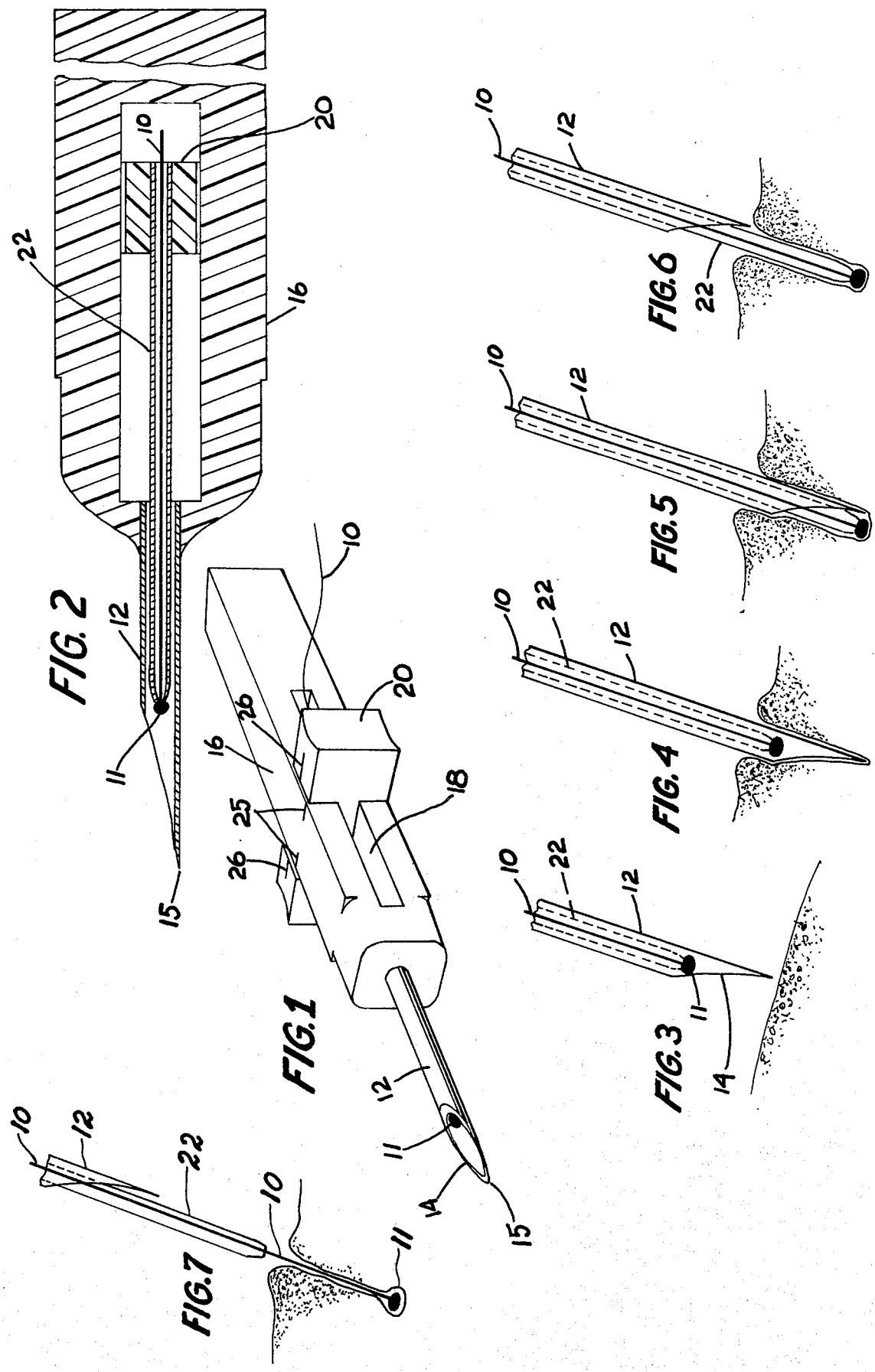

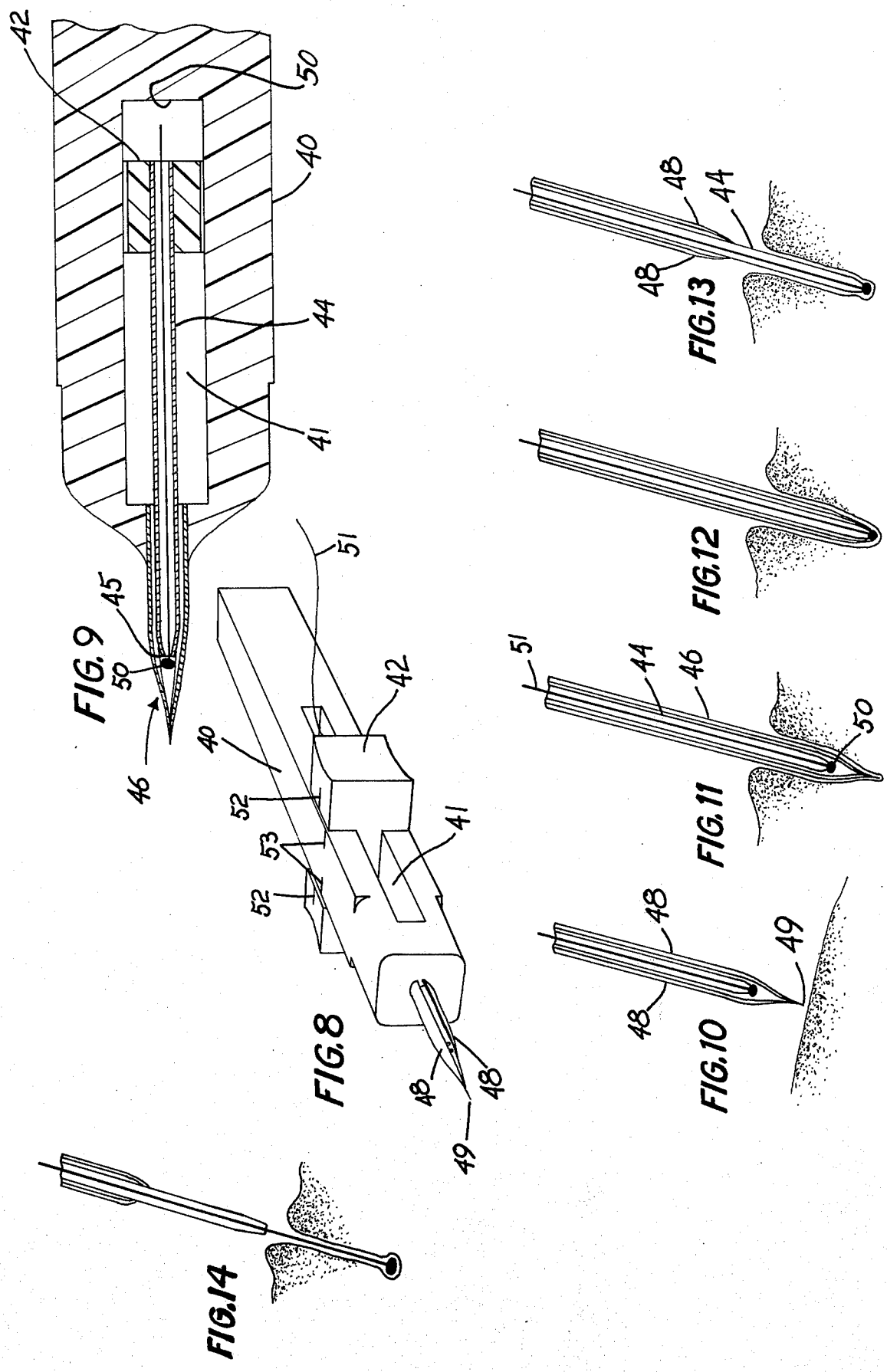

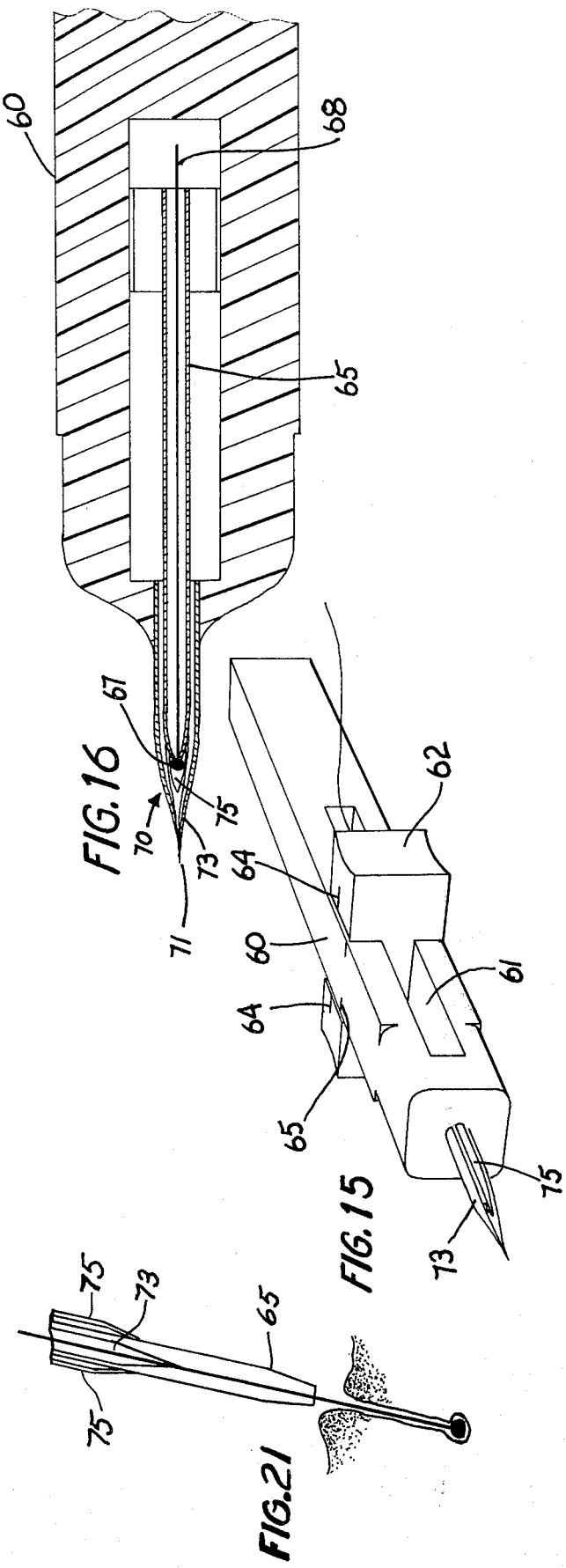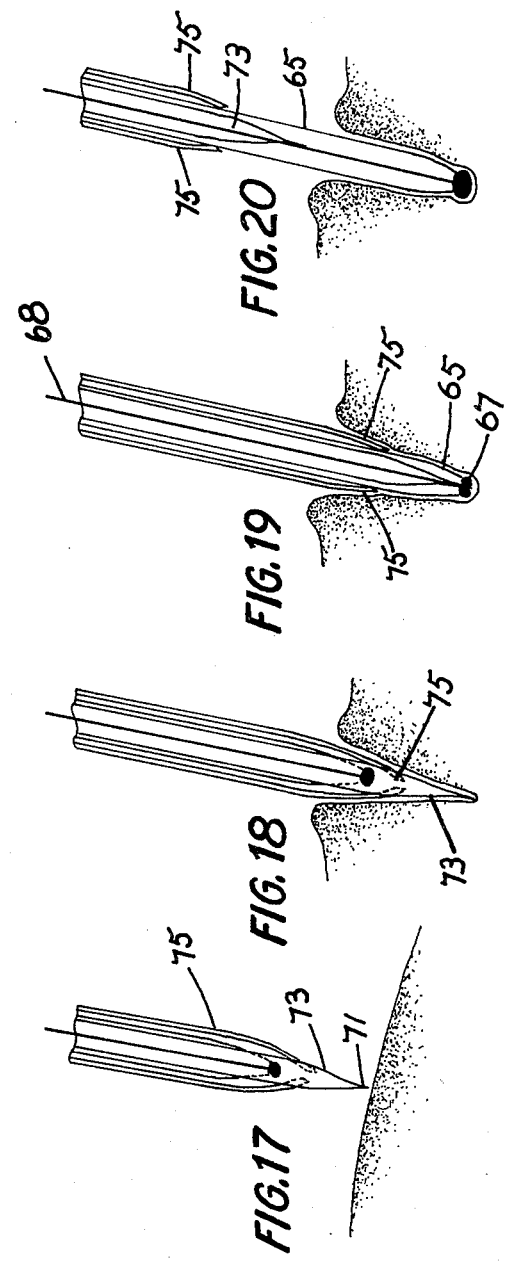

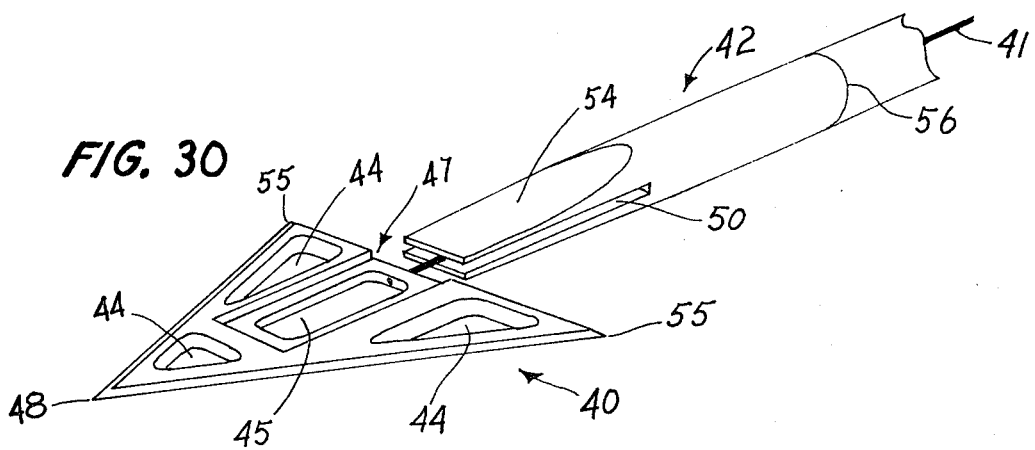
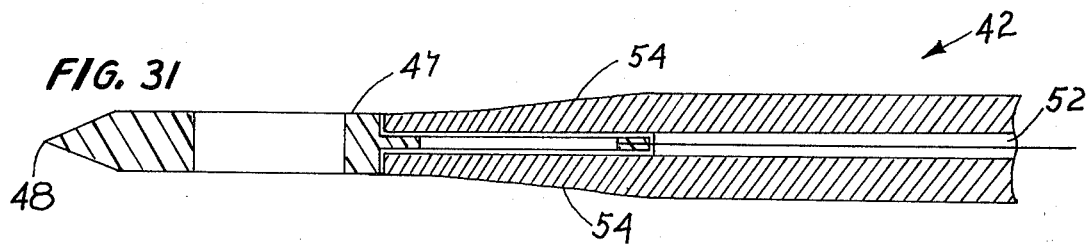
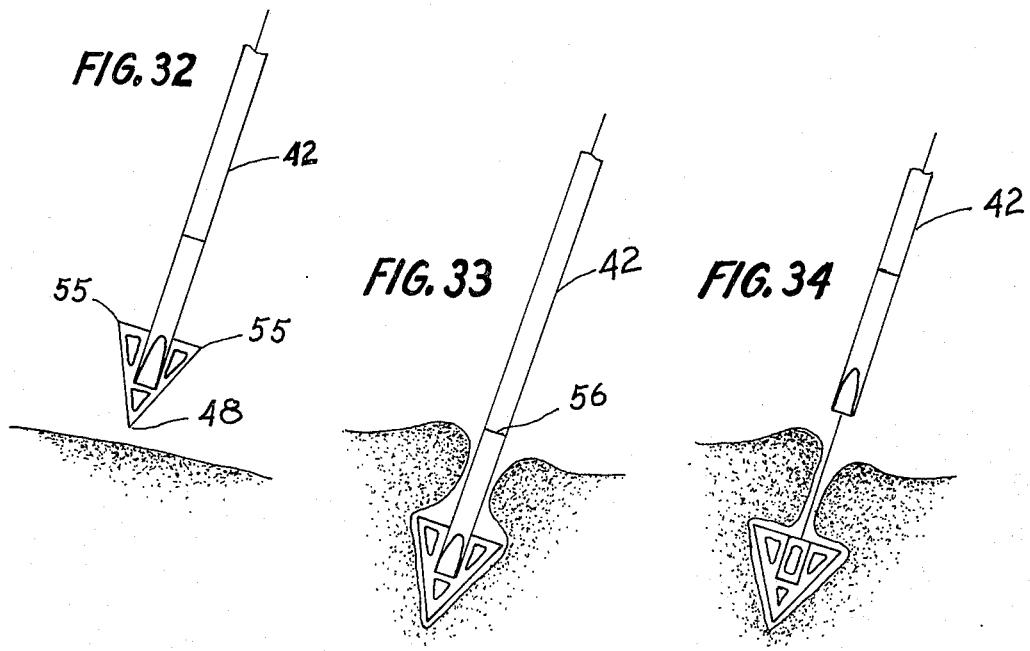

HAIR TRANSPLANT PROCESS

BACKGROUND OF THE INVENTION

This invention relates to methods and apparatuses for implanting natural and synthetic hairs into human skin.

For many years efforts have been made to develop methods and devices for implanting artificial or natural hairs into the scalps of human beings in an effort to eliviate the appearance of baldness. For example, as early as 1913 a relatively complex hair implanting instrument was disclosed in U.S. Pat. No. 1,061,005. This apparatus included a mechanism for advancing a hair through a pair of flexible needle arms in timed sequence with the spreading of the arms. During this same year U.S. Pat. No. 1,059,631 also issued disclosing the use of a hook-type anchor secured to the end of a hair or to a set of hairs to provide a holding action when implanted into a human scalp. These earlier approaches were generally unsuccessful due to the tendency of the hairs to fall out.

In more recent years other methods and apparatuses have been developed in an attempt to improve the hair retention capability of artificially implanted hairs. In U.S. Pat. No. 3,003,155, for example, hair anchors are provided in the form of darts which may be used on either artificial media such as the heads of dolls or, it is claimed, on human scalps. In U.S. Pat. No. 3,062,214 electrically energized electrodes are used in an attempt to improve hair tenacity by creating scar tissue which encompasses the hair anchor. In U.S. Pat. No. 3,596,292 yet another hair anchor is proposed comprising a complex set of loops disposed below a percutaneous portion of the anchor. All of these prior art methods and apparatuses have sought to attain the heretofor illusive goal of providing a relatively simple, practical and economic process of implanting hairs into the scalps of human beings which hairs remain firmly anchored in place for substantial periods of time. These prior attempts, however, have met with only nominal success.

Accordingly, it is a general object of the present invention to provide improved methods and apparatuses for implanting hair into human skin.

More specifically, it is an object of the present invention to provide methods and apparatuses for implanting hair into human skin that remain firmly in place and securely anchored long after the implantation process is performed.

Another object of the invention is to provide a relatively simple method of implanting hair into human skin which method may be performed with facility with but minimal training.

Another object of the invention is to provide a method of implanting hair into human skin which does not tend to inflame or otherwise injure skin tissue.

Yet another object of the invention is to provide apparatuses for implanting hair into human skin of simple and economic construction and which may be readily cleaned for reuse.

SUMMARY OF THE INVENTION

In one form of the invention a method is provided for implanting hair into human skin. The method comprises the steps of inserting an end of a hollow outer needle into the skin to form a pit in the surface thereof, sliding an inner needle within the outer needle to position an end of the inner needle supporting a bulbous end of the hair within the skin pit adjacent the end of the outer needle, and extracting the outer and inner needles from the skin pit.

In another form of the invention a method is provided for implanting hair into human skin which comprises the steps of forming a bulb having at least one passageway therethrough on the end of a hair to be implanted, placing the hair in a first hollow needle with the bulb protruding from an end thereof, and placing the first hollow needle within the second hollow needle with the hair bulb disposed within the second hollow needle, piercing the skin with the second hollow needle, sliding the first hollow needle within the second hollow needle to position the hair bulb adjacent the end of the second hollow needle, and sliding the first and second hollow needles out of the skin.

In another form of the invention apparatus is provided for implanting hair into human skin comprising, in combination, a hollow outer needle having a relatively sharp end for piercing skin, a hollow inner needle slidably disposed within the hollow outer needle and having a centrally apertured relatively blunt end for receiving a hair therethrough and for supporting a bulbous hair end on the surface thereof, and means for moving the inner needle blunt end between positions remote and positions closely adjacent the outer needle sharp end.

In another form of the invention apparatus is provided for implanting hair into human skin comprising a hollow outer needle having a chamfer at one end thereof, an inner needle having an end adapted to support a bulbous end of a hair-like filament slidably disposed within the hollow outer needle, and means for moving the inner needle support end into and out of the hollow outer needle chamfer.

In yet another form of the invention hair implantation apparatus is provided comprising a needle having a slot formed in an injection end thereof from which a passageway extends. A hair-like filament is loosely positioned within the needle passageway with an anchor at one end thereof in the shape of an arrowhead slidably positioned within the needle slot.

BRIEF DESCRIPTION OF THE DRAWING

FIG. 1 is a perspective view of hair implanting apparatus embodying principles of the invention in one preferred form.

FIG. 2 is a cross sectional view of the apparatus shown in FIG. 1.

FIGS. 3–7 are outline drawing views illustrating a sequence of operations in practicing a method of the present invention utilizing the apparatus shown in FIGS. 1 and 2.

FIG. 8 is a perspective view of hair implantation apparatus embodying principles of the invention in another form.

FIG. 9 is a cross sectional view of the apparatus depicted in FIG. 8.

FIGS. 10–14 are outline drawing views illustrating a sequence of operation in practicing a method of the present invention utilizing the apparatus shown in FIGS. 8 and 9.

FIG. 15 is a perspective view of another hair implantation apparatus embodying principles of the invention.

FIG. 16 is a cross sectional view of the apparatus depicted in FIG. 15.

FIGS. 17–21 are outline drawing view of a sequence of operation in practicing a method of the present invention utilizing the apparatus depicted in FIGS. 15 and 16.

FIG. 30 is an exploded, perspective view of yet another hair implantation apparatus embodying principles of the invention.

FIG. 31 is an assembled, side view in cross section of the apparatus depicted in FIG. 30.

FIGS. 32–34 are outline drawing views of a sequence of hair implanting operations utilizing the apparatus shown in FIGS. 30 and 31.

DETAILED DESCRIPTION OF THE DRAWING

Figure 22:
FIGS. 22–29 are perspective views of a hair undergoing a sequence of knotting operations in forming an anchor portion of an end thereof.

Referring now in more detail to the drawing, there is shown in FIGS. 1 and 2 apparatus for implanting a hair 10 having a bulbous end 11 into human skin. The apparatus comprises a tubular outer needle 12 bevelled at one end to form a chamfer 14 at an injection end thereof forming a sharp point 15. The outer needle is rigidly mounted to a handle 16 having a slot 18 formed through a central portion thereof. Within this slot is slidably mounted another handle or actuator 20 of H-shaped configuration to which a hollow inner needle 22 is rigidly mounted in frictionally sliding disposition within outer needle 12. The end of needle 22 distal actuator 20 is of bullet-shaped configuration and thus possesses a relatively blunt end in comparison with the sharp end of needle 12. A broken line 25 is marked upon the top of handle 16 and a line 26 marked atop actuator 20 to provide an indexing guide for positioning the two handles relative one another.

Figure 23:
Figure 24:
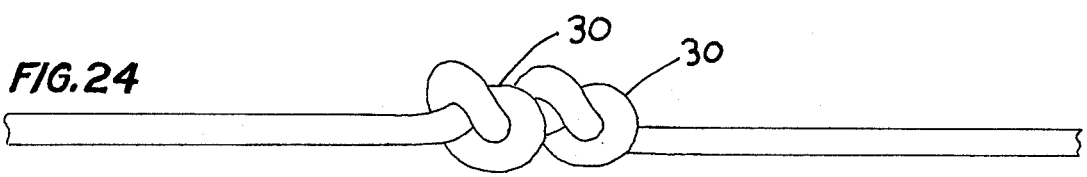
Figure 25:
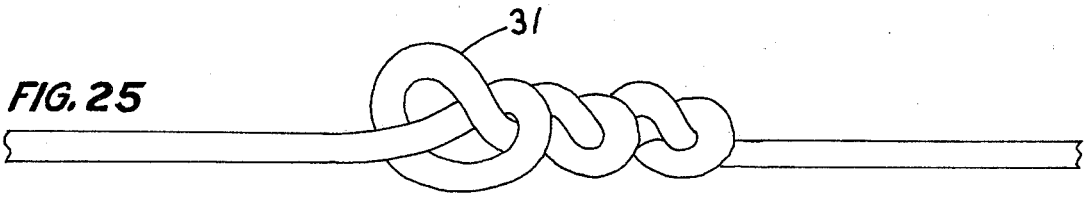
Figure 26:
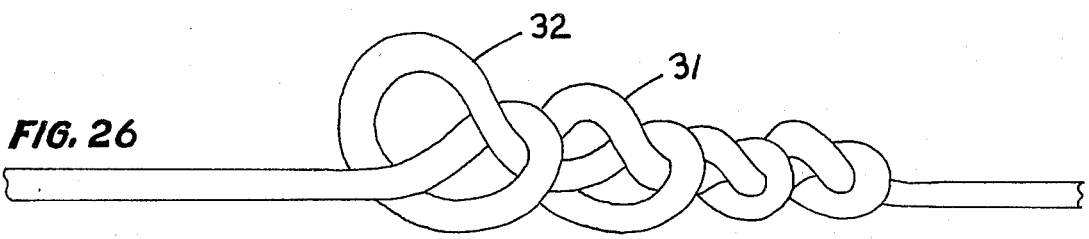
Figure 27:
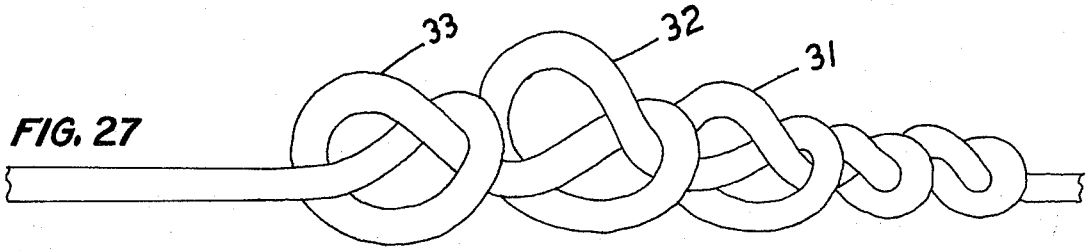
Figure 28:
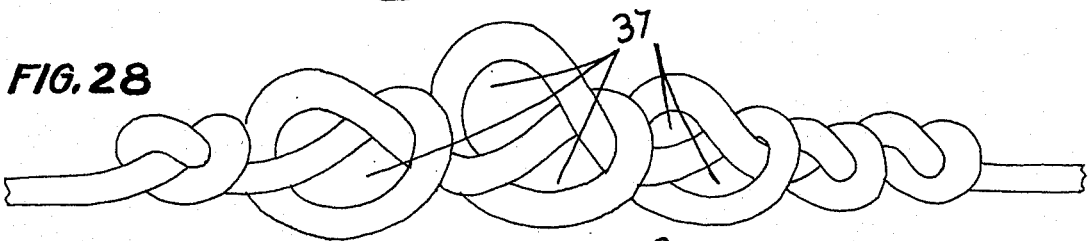
Figure 29:
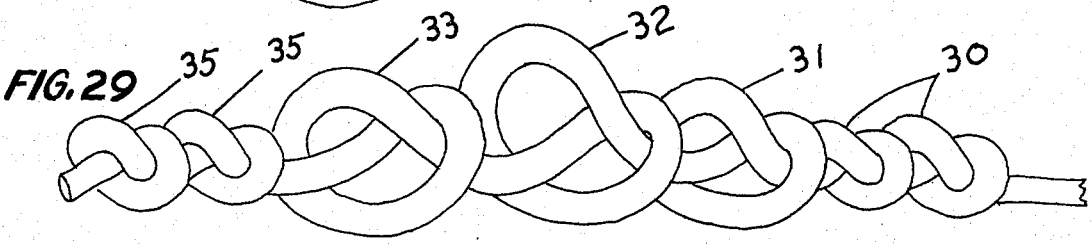

In performing the implantation operation a bulbous end is first formed on the synthetic or natural hair 10 with a set of interstices or passageways therethrough. A preferred formation of this bulbous end is shown in FIGS. 22–29 where the end is seen to be formed by tying a series of overhand knots or loops with the first two knots 30 being taut, with the third knot 31 being loose, with the fourth knot 32 being even looser than 31, with the fifth knot 33 having a looseness approximating that of knot 31 and with the sixth and seventh knots 35 being taut. So tied, the bulbous end is provided with a set of interstices or passageways 37 through hair loops pervious to the growth of skin tissue which set is maintained in place by the two taut knots at each end of the series of three open knots. Alternatively, the bulbous end may be composed of silicone.

After the bulb has been formed on the hair end actuator 20 is positioned forwardly within slot 18 to provide ready access to the inner needle and the hair then inserted through the channel of inner needle 22 bringing the bulbous end onto the relatively blunt end of the needle. With the hair in place the actuator is moved rearwardly to the end of the slot by manual manipulation and handle 16 then urged towards the human skin bringing outer needle chamfer 14 into close proximity with the skin as shown in FIG. 3. The outer needle is then injected into the skin as shown in FIG. 4 creating the pit in the skin approximating the shape of chamfer 14. With the pit so formed actuator 20 is moved forwardly towards the skin until lines 26 are into registry with lines 25 which positions the relatively blunt end of the needle closely adjacent the outer needle tip 15 as shown in FIG. 5. In performing this operation the skin pit is enlarged slightly to accomodate the presence of the inner needle blunt end. Following this, actuator 20 is urged forwardly towards the end of the slot proximal outer needle end 15 while simultaneously urging handle 16 away from the skin which action serves to extract the outer needle from the skin pit while leaving the inner needle residing therewithin as shown in FIG. 6. This extraction of the outer needle causes the walls of the skin pit to close inwardly towards the inner needle which is then removed by moving handle 16 further away from the skin without necessarily imparting any further relative movement between the actuator and handle. This causes the inner needle also to be removed from the skin pit leaving the hair firmly implanted therewithin with the continually encroaching walls of the pit sealing about bulbous end 11. Subsequently, the skin tissue will also grow through interstices 37 rendering the implanted hair even more secure and tenacious.

Referring next to FIGS. 8 and 9 another embodiment of the invention is shown comprising a handle 40 having a slot 41 therein through which another H-shaped actuator 42 is slidably disposed in frictional engagement within handle 40 and with the actuator and handle again having indexing lines printed thereatop. To actuator 42 is rigidly mounted an inner, tubular needle 44 having a relatively blunt end 45 slidably disposed within an outer needle 46 that is rigidly secured to the handle. The inner needle, actuator and handle are thus seen to be of the same construction as that shown in FIGS. 1 and 2 whereas the outer needle 46 is seen to be of split injection type construction comprising a pair of arcuate prongs 48 spring biased into mutual engagement at their relatively sharp, mutually abutting ends 49.

In operation here actuator 42 is slid to the rear end 50 of slot 41 once needle 44 is loaded with a hair as previously described and handle 40 then moved towards the human skin to position outer needle sharp end 49 closely adjacent the skin as shown in FIG. 10. From this position handle 40 is urged forwardly injecting the split outer needle into the skin to form a skin pit in which both the outer needle and the blunt end portion of inner needle 44 are located. Next, actuator 42 is moved forwardly away from slot end 50 bringing lines 52 atop the actuator into registry with lines 53 on the handle. This action causes inner needle 44 to slide forwardly within the outer needle prongs 48. This action brings the outer peripheral portion of the blunt end of needle 44 into engagement with the insides of prongs 48 thereby forcing them radially outward from the coincident axes of the two needles. In this manner the prongs 48 are forced radially apart prior to any engagement of the bulbous end portion 50 of hair 51 seated upon the inner peripheral portion of the needle blunt end with the prongs. Thus, the centrally apertured annular portion of the blunt end serves both to support the bulbous end 50 of the hair and to cam apart the prongs of the outer needle.

At this point the relative positions of the two needles within the skin pit are depicted in FIG. 12. Next, actuator 42 is urged to the opposite end of the slot from slot end 50 while handle 40 is simultaneously moved away from the skin. This causes the outer needle prongs 48 to slide up upon the outside of inner needle 44 thereby extracting the outer needle from the skin pit as shown in FIG. 13. Finally, the handle 40 is moved further away from the skin without necessarily imparting any further relative movement between the two needles thereby extracting the inner needle too from the skin pit leaving the hair firmly implanted.

Referring next to FIGS. 15 and 16, yet another embodiment of the invention is shown comprising a handle 60 having a slot 61 in which is slidably disposed an actuator 62 of generally H-shaped configuration having a pair of aligned marks 64 thereatop adapted to be aligned with lines 65 atop handle 60. As in the previously described embodiments actuator 62 supports a tubular needle 65 having a relatively blunt end for supporting a bulbous end 67 of a hair 68. Handle 60 supports a split-injection type needle 70 having a relatively sharp end 71. This split-injection needle comprises two arcuate, resilient prongs 73 spring biased into mutual engagement at points 71 plus a second pair of arcuate, resilient prongs 75 having their ends spaced apart and longitudinally offset from points 71 of the other pair of prongs. The inner and outer needles may be moved relative to one another by the movement of actuator 62 within slot 61 as described in the discussion of the previous embodiments.

The relative positioning of the needles within the skin is illustrated in FIGS. 17–21 wherein in FIG. 17 outer needle end 71 is shown positioned closely adjacent the skin and in FIG. 18 injection of both pairs of outer needle prongs has been completed to create a skin pit thereabout. That the two pairs of prongs separate along planes oriented normal to one another serves to create a generally cylindrical pit in the skin which subsequently minimizes hair end contact with the pit walls. Following this inner needle 65 is advanced into engagement with prongs 75 forcing them outwardly apart as shown in FIG. 19. Continuation of this advancement of the inner needle enlarges the cavity somewhat in positioning the bulbous end 67 of hair 68 adjacent sharp point 71 of the outer needle. In this the relatively blunt end of the inner needle also serves to force apart the resilient prongs 73 enabling the bulbous end of the hair to be seated therebetween. Next, the outer needle is pulled away from the skin over the surface of the inner needle the presence of which continues to separate both pairs of the spring biased prongs of the outer needle as illustrated in FIG. 20. Finally, inner needle 65 is also pulled from the skin pit as shown in FIG. 21 leaving the hair i planted firmly within the skin.

Referring to FIGS. 30 and 31 still another embodiment of the invention is illustrated wherein a needle 42 is seen to support a hair 41 having a flat triangular anchor 40 formed on an end thereof in the general shape of an arrowhead having a pointed injection tip 48 and two sharp wing tips 55. Preferably, both the hair and anchor are unitarily composed of silicone. Alternatively, the hair may be natural and joined to the anchor during anchor molding.

The injection end of needle 42 has a slot 50 from which a tubular passageway 52 extends. This passageway is seen to extend along the axis of the generally cylindrical needle. Alternatively, the passageway may curve off of the needle axis up to the cylindrical surface of the needle, or may even communicate continuously with that surface in the form of an elongated trough. A guide mark 56 is also provided encircling the needle body.

The injection end of the needle is further seen to have two opposing chamfers 54 overlaying slot 50. These chamfers taper the cylindrical needle end surface to a flat tip having an overall thickness approximating that of anchor 40. A central portion of the arrowhead-shaped anchor is provided with a recess 47 in each flat surface thereof of depth slightly greater than the thickness of each needle tip prong provided between chamfer 54 and slot 50. These dimensional relations between the hair anchor and needle tip enable the anchor to be slidably supported in the needle slot with the flat surfaces of the needle tip and anchor to be substantially coplanar as seen in FIG. 31. The arrowhead-shaped hair anchor is also provided with a central opening 45 and three triangular openings 44 pervious to the growth of skin tissue.

For operation, hair 41 is slid through the needle tip and into passageway 52 bringing the anchor recess 47 into slot 50. With the hair and anchor so loaded onto the needle the assembly appears as shown in FIG. 31. The loaded needle is then positioned for skin injection as shown in FIG. 32. Next, the loaded needle is injected as shown in FIG. 33 bringing the arrowhead-shaped hair anchor fully into the skin when guide mark 56 is located at skin level. The unique loading of the hair anchor and needle with the flat surfaces of both substantially coplanar facilitates skin penetration due to the firm but sliding support arrangement. Quickly, the skin tissue closes about the two wing tips 55 of the anchor. Needle 42 is then extracted from the skin during which operation hair 41 remains stationary, sliding freely within passageway 52 of the departing needle. Subsequently, the anchor will become more firmly set by the growth of skin tissue through the openings therein.

It should be understood that the just described embodiments merely serve to illustrate principles of the invention in preferred forms. Many modifications may, of course, be made thereto without departure from the spirit and scope of the invention as set forth in the following claims:

What is claimed is:
1. A method of implanting hair in human skin comprising the steps of:
   a. tightly tieing two end loop members and loosely tieing at least one intermediate open loop member in a series of loops on the end of a hair thereby forming a bulb having at least one passageway therethrough on the end of a hair to be implanted;
   b. placing the hair in a 1st hollow needle with the bulb positioned adjacent an end thereof;
   c. placing the 1st hollow needle within a 2nd hollow needle with the hair bulb disposed within the 2nd hollow needle;
   d. piercing the skin with the 2nd hollow needle;
   e. sliding the 1st hollow needle within the 2nd hollow needle to position the hair bulb adjacent the end of the 2nd hollow needle; and
   f. sliding the 1st and 2nd hollow needles out of the skin.
2. The hair implantation method of claim 1 Comprising the step (f) sliding the 1st and 2nd hollow needles over the hair out from the human skin simultaneously.
3. The hair implantation method of claim 1 Comprising the step (f) sliding the 2nd hollow needle over the hair out from the human skin and subsequently sliding the 1st hollow needle over the hair out from the human skin.
4. Apparatus for implanting hair in human skin comprising in combination, a 1st handle defining a slot, a hollow outer needle secured to said 1st handle and having a relatively sharp end for piercing skin; a 2nd handle of substantially H-shaped configuration mounted in mutual sliding engagement in said 1st han- dle slot; a hollow inner needle secured to said 2nd handle and slidably disposed within said hollow outer needle and having a centrally apertured relatively blunt end for receiving a hair therethrough and for supporting a bulbous hair end on the surface thereof, and means for moving said inner needle blunt end between positions extending beyond said hollow needle sharp end and positions within said outer needle sharp end.

5. Hair implantation apparatus in accordance with claim 4 comprising indexing means for indicating relative axial positions of said inner needle with respect to said outer needle.

6. In the method of implanting a human hair into skin by which a hollow needle is inserted into skin to form a pit in the surface thereof and a bulbous end of a hair supported within the hollow needle is positioned within the skin pit, the improvement comprising forming the bulbous end on the human hair end prior to implantation by tying the human hair end into a loop with a spacial interstice through which skin tissue may subsequently grow and thereby tenaciously anchor the hair.

* * * * *